United States Patent
Brown

(10) Patent No.: US 6,414,227 B1
(45) Date of Patent: Jul. 2, 2002

(54) INBRED CORN LINE IT302

(75) Inventor: Kevitt D. Brown, West Lafeyette, IN (US)

(73) Assignee: FFR Cooperative, Inc., Battle Ground, IN (US)

( * ) Notice: Subject to any disclaimer, the term of this patent is extended or adjusted under 35 U.S.C. 154(b) by 0 days.

(21) Appl. No.: 09/250,810

(22) Filed: Feb. 17, 1999

(51) Int. Cl.⁷ .............................. A01H 1/00; A01H 1/02; A01H 5/00; A01H 5/10; C12N 5/04
(52) U.S. Cl. .................... 800/320.1; 800/263; 800/265; 800/274; 800/275; 800/278; 800/300.1; 800/301; 800/302; 800/303; 435/412; 435/419; 435/421; 435/424; 435/430; 435/430.1
(58) Field of Search ............................... 800/320.1, 275, 800/271, 303, 265, 263, 274, 301, 302, 300.1, 278; 435/412, 424, 430, 430.1, 419, 421; 536/23.1

(56) References Cited

PUBLICATIONS

Plant Variety Protection Certificate for LH195.

*Primary Examiner*—David T. Fox
(74) *Attorney, Agent, or Firm*—Rothwell, Figg, Ernst & Manbeck

(57) ABSTRACT

An inbred corn line, designated IT302, is disclosed. The invention relates to the seeds of inbred corn line IT302, to the plants of inbred corn line IT302 and to methods for producing a corn plant produced by crossing the inbred line IT302 with itself or another corn line. The invention further relates to hybrid corn seeds and plants produced by crossing the inbred line IT302 with another corn line.

29 Claims, No Drawings

INBRED CORN LINE IT302

BACKGROUND OF THE INVENTION

The present invention relates to a new and distinctive corn inbred line, designated IT302. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated IT302. This invention thus relates to the seeds of inbred corn line IT302, to the plants of inbred corn line IT302 and to methods for producing a corn plant produced by crossing the inbred line IT302 with itself or another corn line. This invention further relates to hybrid corn seeds and plants produced by crossing the inbred line IT302 with another corn line.

The inbred corn plant of the invention may further comprise or have a cytoplasmic factor that is capable of conferring male sterility. Parts of the corn plant of the present invention are also provided, such as e.g., pollen obtained from an inbred plant and an ovule of the inbred plant.

In another aspect, the present invention provides for single gene converted plants of IT302. The single transferred gene may preferably be a dominant or recessive allele. Preferably, the single transferred gene will confer such traits as male sterility, herbicide resistance, insect resistance, resistance for bacterial, fungal or viral disease, male fertility, enhanced nutritional quality and industrial usage. The single gene may be a naturally occurring maize gene or a transgene introduced through genetic engineering techniques.

In another aspect, the present invention provides plant cells for use in tissue culture of inbred corn plant IT302. The tissue culture will preferably be capable of regenerating plants having the physiological and morphological characteristics of the foregoing inbred corn plant and of regenerating plants having substantially the same genotype as the foregoing inbred corn plant. Preferably, the regenerable cells in such tissue cultures will be embryos, protoplasts, meristematic cells, callis, pollen, leaves, anthers, roots, root tips, silk flowers, kernels, ears, cobs, husks or stalks. Still further, the present invention provides corn plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Predicted RM

This trait for a hybrid, predicted relative maturity (RM), is based on the harvest moisture of the grain. The relative maturity rating is based on a known set of checks and utilizes conventional maturity systems such as the Minnesota Relative Maturity Rating System.

MN RM

This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre)

The yield in bushels/acre is the actual yield of the grain at harvest adjusted to 15.5% moisture.

Moisture

The moisture is the actual percentage moisture of the grain at harvest.

GDU Silk

The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are:

$$GDU = \frac{(Max.+Min)}{2} - 50.$$

The highest maximum used is 86° F. and the lowest minimum used is 50° F. For each hybrid, it takes a certain number of GDUs to reach various stages of plant development. GDUs are a way of measuring plant maturity.

Stalk Lodging

This is the percentage of plants that stalk lodge, i.e., stalk breakage, as measured by either natural lodging or pushing the stalks determining the percentage of plants that break off below the ear. This is a relative rating of a hybrid to other hybrids for standability.

Root Lodging

The root lodging is the percentage of plants that root lodge; i.e., those that lean from the vertical axis at an approximate 30° angle or greater would be counted as root lodged.

Plant Height

This is a measure of the height of the hybrid from the ground to the tip of the tassel, and is measured in centimeters.

Ear Height

The ear height is a measure from the ground to the ear node attachment, and is measured in centimeters.

Dropped Ears

This is a measure of the number of dropped ears per plot, and represents the percentage of plants that dropped an ear prior to harvest. Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing

This is a process in which a breeder repeatedly crosses hybrid progeny back to one of the parents, for example, a first generation hybrid $F_1$ with one of the parental genotypes of the $F_1$ hybrid.

Essentially all the Physiological and Morphological Characteristics

A plant having essentially all the physiological and morphological characteristics means a plant having the physiological and morphological characteristics except for also having the trait derived from the converted gene.

Quantitative Trait Loci (QTL)

Quantitative Trait Loci (QTL) refers to genetic loci that control, to some degree, numerically representable traits that are usually continuously distributed.

Regeneration

Regeneration refers to the development of a plant from tissue culture.

Single Gene Converted

Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique.

DETAILED DESCRIPTION OF THE INVENTION

Inbred corn line IT302 is a yellow dent corn with superior characteristics, and provides an excellent parental line in crosses for producing first generation ($F_1$) hybrid corn.

IT302 is a corn inbred line developed from the backcross population ((A6321T ×F406)×F406)×F406)). F406 is an FFR proprietary line of a Southern U.S. origin. IT302 was developed using an ear-row pedigree method of breeding. Selection during the backcross procedure was based on tolerance to spray applications of Pursuit™ herbicide and phenotypic resemblance to F406. Selfing and selection were practiced for six generations in the development of IT302. Selections were made for earing ability and general plant health of the inbred per se, as well as yield, disease tolerance and agronomic ability of the hybrids resulting from crosses to various tester male inbreds.

IT302 is used as a male in hybrid production and confers tolerance to imidazolinone herbicides to its hybrids. IT302 also has a high level of resistance to Gray Leaf Spot (*Cercospora zeae-maydis*) disease and moderate resistance to Maize Dwarf Mosaic Virus complex. These hybrids are tall with girthy ears. Yields are similar to competitive hybrids in the same maturity class. IT302 has very good tonnage and fiber digestibility for silage use.

Inbred corn line IT302 has the following morphologic and other characteristics (based primarily on data collected at West Lafayette, Ind.).

VARIETY DESCRIPTION INFORMATION

1. TYPE: Dent
2. MATURITY:
   Best adapted to the Midsouth and Southeast
   Heat units to mid-pollen: 1509 GDU
3. PLANT:
   Plant Height (to tassel tip): 165 cm
   Average number of Tillers: 0
   Average Number of Ears per Stalk: 1
   Cytoplasm type: normal
   Ear height (to base of top ear): 57 cm
4. TASSEL:
   Number of Lateral Branches: 18
   Branch Angle from Central Spike: 45 degrees
   Pollen Shed (Rate on scale from 0=male sterile to 9=heavy shed): 5
   Anther Color: Pink
5. EAR: (Husked Ear Data)
   Husk color: Buff
   Silk color: Green
   Ear Taper: Blocky
   Position of shank: Upright
6. KERNEL: (Dried)
   Hard Endosperm Color: Yellow
   Endosperm Type: Normal Starch
7. COB:
   Color: Pink This invention is also directed to methods for producing a corn plant by crossing a first parent corn plant with a second parent corn plant, wherein the first or second corn plant is the inbred corn plant from the line IT302. Further, both first and second parent corn plants may be from the inbred line IT302. Therefore, any methods using the inbred corn line IT302 are part of this invention: selfing, backcrosses, hybrid breeding, and crosses to populations. Any plants produced using inbred corn line IT302 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g. IT302) or hybrid plant of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green & Rhodes (1982) and Duncan et al., (1985). The study by Duncan et al. (1985) indicates that 97 percent of cultured plants produced call capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al. (1988); Rao et al.

(1986); and Conger et al. (1987), the disclosures of which are incorporated herein by reference. Regenerable cultures may be initiated from immature embryos as described in PCT publication WO 95/06128, the disclosure of which is incorporated herein by reference. Thus, another aspect of this invention is to provide for cells which upon growth and differentiation produce the inbred line IT302.

IT302 is similar to LH195, however there are numerous differences including IT302 flowers earlier than LH195 and is taller with wider leaves than LH195.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run at the West Lafayette, Indiana breeding station. The inbred was evaluated further as a line and in numerous crosses at other breeding stations across the Corn Belt. The inbred has proven to have a very good combining ability in hybrid combinations.

The inbred line has shown uniformity and stability for the traits, as described in the variety description information. It has been self-pollinated a sufficient number of generations with careful attention to uniformity of plant type. The line has been increased with continued observation for uniformity.

TABLES

In the tables that follow, the traits and characteristics of inbred corn line IT302 are given in hybrid combination. The data collected on inbred corn line IT302 is presented for the key characteristics and traits. The tables present yield test information about IT302. IT302 was tested in several hybrid combinations at numerous locations. Information about these hybrids, as compared to several check hybrids, is presented in Table 1.

Information for the pedigree includes:

In column 1, the number of locations tested (#LOC) is shown. In column 2, the first genotype listed (in row 1) is the hybrid containing IT302 and the remaining genotypes listed are comparison varieties of similar maturities. Columns 3 and 4 show the bushels/acre (YIELD) and percent moisture (%H2O) for each genotype. In columns 5 and 6 information for the genotype includes: root lodging (ROOT) scores and stalk lodging (STALK). Columns 7 and 8 indicate ear height (E.HT) and plant height (P.HT.). Columns 9 and 10 indicate gray leaf spot and virus complex scoring.

The hybrid listed under the hybrid containing IT302 is considered a check hybrid. This check hybrid is compared to the hybrid containing the inbred IT302.

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehlman & Sleper, 1994; Fehr. 1978). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent plant.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected in the development of a new inbred but

TABLE 1

IT302 HEAD TO HEAD COMPARISONS in 1997

| #LOC | PEDIGREE | YIELD | % H2O | % ROOT | % STALK | E.HT. | P.HT. | Gray Leaf Spot | Virus Complex |
|---|---|---|---|---|---|---|---|---|---|
| 8 | LH213 × IT302 | 148.6 | 18.7 | 4.4 | 3.1 | 4.7 | 11.0 | 3.7 | 4.8 |
| 8 | Pioneer 3163 | 144.6 | 18.8 | 1.0 | 2.9 | 4.5 | 10.5 | 4.7 | 5.2 |
| 8 | FFR 797IT | 132.3 | 18.9 | 1.6 | 2.2 | 4.3 | 10.3 | 6.7 | 6.8 |
| 8 | DeKalb 683 | 139.6 | 19.6 | 2.5 | 2.1 | 5.1 | 11.0 | 3.0 | 2.4 |
| 8 | LH213 × F406 | 147.7 | 20.5 | 2.0 | 1.6 | 4.9 | 11.2 | 1.0 | 5.4 | that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. No. 5,777,196, the disclosure of which is specifically hereby incorporated by reference.

A further aspect of the invention relates to tissue culture of corn plants designated IT302. As used herein, the term "tissue culture" indicates a composition isolated cells of the same or a different type or a collection of such cells organized into parts of a plant. Exemplary types of tissue cultures are protoplasts, calli, plant clumps and plant cells that can generate tissue culture that are intact in plants or parts of plants, such as embryos, pollen, flowers, kernels, ears, cobs, leaves, husks, stalks, roots, root tips, anthers, silk and the like. In a preferred embodiment, tissue culture is embryos, meristematic, protoplast, meristematic cells, pollen, leaves or anthers. Means for preparing and maintaining plant tissue culture are well known in the art. By way of example, a tissue culture comprising organs such as tassels or anthers, has been used to produce regenerated plants (See, U.S. Pat. No. 5,445,961 and U.S. Pat. No. 5,322,789, the disclosures of which are incorporated herein by reference).

DEPOSIT INFORMATION

A deposit of the FFR Cooperative inbred corn line IT302 disclosed above and recited in the appended claims has been made with the American Type Culture Collection (ATCC), 10801 University Boulevard, Manassas, Va. 20110. The date of deposit was Apr. 3, 2002. The deposit of 2,500 seeds were taken from the same deposit maintained by FFR Cooperative since prior to the filing date of this application. All restrictions upon the deposit have been removed, and the deposit is intended to meet all of the requirements of 37 C.F.R. §1.801–1.809. The ATCC accession number is PTA-4198. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated IT302, wherein a sample of said seed has been deposited under ATCC Accession No. PTA-4198.

2. A plant or its parts produced by growing the seed of claim 1.

3. Pollen of the plant of claim 2.

4. An ovule of the plant of claim 2.

5. A corn plant having all of the physiological and morphological characteristics of the plant of claim 2, or its parts.

6. Tissue culture of the seed of claim 1.

7. A corn plant regenerated from the tissue culture of claim 6, wherein said corn plant is capable of expressing all the physiological and morphological characteristics of inbred corn line IT302.

8. Tissue culture of regenerable cells of the plant or its parts of claim 2.

9. The tissue culture of claim 8, wherein the regenerable cells are embryos, meristematic cells, pollen, leaves, anthers, roots, root tips, silk, flowers, kernels, ears, cobs, husks, stalks or protoplasts or calli derived therefrom.

10. A corn plant regenerated from the tissue culture of claim 9, wherein said corn plant is capable of expressing all the physiological and morphological characteristics of inbred corn line IT302.

11. A method for producing a hybrid corn seed comprising crossing a first inbred parent corn plant with a second inbred parent corn plant and harvesting the resultant hybrid corn seed, wherein said first or second parent corn plant is the corn plant of claim 2.

12. A hybrid seed produced by the method of claim 11.

13. A hybrid plant or its parts produced by growing said hybrid corn seed of claim 11.

14. Seed produced from said hybrid plant of claim 13.

15. A method for producing a hybrid corn seed comprising crossing an inbred plant according to claim 2 with another, different corn plant.

16. A hybrid seed produced by the method of claim 15.

17. A hybrid plant, or its parts, produced by growing said hybrid corn seed of claim 16.

18. Seed produced from said hybrid plant of claim 17.

19. The corn plant having all of the physiological and morphological characteristics of the plant of claim 2 and further comprising a single gene conversion.

20. The corn plant of claim 19, further comprising a cytoplasmic factor conferring male sterility.

21. The single gene conversion corn plant of claim 19, where the gene is gene which is introduced by transgenic methods.

22. The single gene conversion corn plant of claim 19, where the gene is a dominant allele.

23. The single gene conversion corn plant of claim 19, where the gene is a recessive allele.

24. The single gene conversion corn plant of claim 19, where the gene confers herbicide resistance.

25. The single gene conversion corn plant of claim 19, where the gene confers insect resistance.

26. The single gene conversion corn plant of claim 19, where the gene confers resistance to bacterial, fungal, or viral use.

27. The single gene conversion corn plant of claim 19, where the gene confers male sterility.

28. The single gene conversion corn plant of claim 19, where the gene confers waxy starch.

29. The single gene conversion corn plant of claim 19, where the gene confers improved nutritional quality.

* * * * *